United States Patent
Dhamane et al.

(10) Patent No.: US 10,864,207 B2
(45) Date of Patent: Dec. 15, 2020

(54) METHOD OF TREATING ENDOTHELIAL DYSFUNCTION

(71) Applicant: Celagenex Research (India) Pvt. Ltd., Thane (IN)

(72) Inventors: Dhiraj Dhamane, Kalyan-Thane (IN); Rajendra Prasad Tongra, Jaipur (IN)

(73) Assignee: Celagenex Research (India) Pvt. Ltd., Thane (IN)

( * ) Notice: Subject to any disclaimer, the term of this patent is extended or adjusted under 35 U.S.C. 154(b) by 0 days.

(21) Appl. No.: 16/733,131

(22) Filed: Jan. 2, 2020

(65) Prior Publication Data

US 2020/0222383 A1 Jul. 16, 2020

(30) Foreign Application Priority Data

Jan. 2, 2019 (IN) .............................. 201921000093

(51) Int. Cl.
| | |
|---|---|
| *A61K 36/21* | (2006.01) |
| *A61K 31/455* | (2006.01) |
| *A61K 9/00* | (2006.01) |
| *A61K 33/00* | (2006.01) |

(52) U.S. Cl.
CPC .......... *A61K 31/455* (2013.01); *A61K 9/0056* (2013.01); *A61K 33/00* (2013.01); *A61K 36/21* (2013.01)

(58) Field of Classification Search
None
See application file for complete search history.

(56) References Cited

U.S. PATENT DOCUMENTS

| | | | |
|---|---|---|---|
| 9,833,426 B2 | 12/2017 | Morita et al. | |
| 10,653,737 B1 * | 5/2020 | Dhamane | A61K 9/0053 |
| 2010/0120726 A1 * | 5/2010 | Bender | A61K 31/401 514/162 |
| 2011/0082177 A1 * | 4/2011 | Gebicki | A61P 9/14 514/355 |
| 2020/0108110 A1 * | 4/2020 | Antony | A61P 43/00 |

FOREIGN PATENT DOCUMENTS

| | | |
|---|---|---|
| JP | 2012041296 A | 3/2012 |
| JP | 2013227256 A | 11/2013 |

OTHER PUBLICATIONS

Jin Bo Su, "Vascular endothelial dysfunction and pharmacological treatment", World J Cardiol. 7(11): 719-741 (2015).
Zhou, S., et al., "Repression of P66Shc Expression by SIRT1 Contributes to the Prevention of Hyperglycemia-Induced Endothelial Dysfunction", Circ Res. 109(6):639-648 (2011).
Chlopicki, S., et al., "1-Methylnicotinamide (MNA), a primary metabolite of nicotinamide, exerts anti-thrombotic activity mediated by a cyclooxygenase-2/prostacyclin pathway", Br J Pharmacol. 152(2): 230-239 (2007).
Turck, D., et al., "Safety of 1-methylnicotinamide chloride (1-MNA) as a novel food pursuant to Regulation (EC) No. 258/97", EFSA Journal, 15(10):5001; p. 1-16 (2017). www.efsa.europa.eu/efsajournal.
Lundberg, J. O., and Mirco Govoni, "Inorganic Nitrate is a Possible Source for Systemic Generation of Nitric Oxide", Free Radical Biol Med. vol. 37(3); p. 395-400 (2004).
Champion, H.C., et al., "Phosphodiesterase-5A dysregulation in penile erectile tissue is a mechanism of priapism", PNAS 102(5):1661-1666 (2005). www.pnas.org/cyi/doi/10.1073/pnas.0407183102.

* cited by examiner

*Primary Examiner* — Ralph J Gitomer
(74) *Attorney, Agent, or Firm* — Melissa M. Hayworth; E. Joseph Gess

(57) ABSTRACT

The present invention herein discloses potent synergistic compositions of vasoactive mediators enhancers for improving vascular endothelial function. Particularly, the invention relates to synergistic nutritional composition comprising exogenous blend of $N^1$-methyl nicotinamide chloride and standardized red spinach extract enriched with nitrate content along with pharmaceutically acceptable excipients, wherein $N^1$-methyl nicotinamide salt and standardized red spinach extract enriched with nitrate content are present in the ratio of 1:0.5 to 1:8; and $N^1$-methyl nicotinamide chloride and nitrate of standardized red spinach extract, are present in the ratio of 1:0.1 to 1:1. The present synergistic composition is useful for treating endothelial dysfunction such as hypertension, atherosclerosis, thrombosis, myocardial infarction, heart injury.

9 Claims, 3 Drawing Sheets

METHOD OF TREATING ENDOTHELIAL DYSFUNCTION

TECHNICAL FIELD OF THE INVENTION

The present invention relates to potent synergistic compositions of vasoactive mediator enhancers for improving vascular endothelial function.

Particularly, the invention relates to synergistic composition of vasoactive mediators, preferably prostanoids and nitric oxide enhancers.

Most particularly, the invention relates to synergistic composition of vasoactive mediator enhancers, wherein vasoactive prostanoid i.e. prostacyclin (PGI2) enhancing agent is N-1-methyl nicotinamide salt and nitric oxide enhancer is inorganic nitrate/nitrite extracted from natural source, along with pharmaceutically acceptable excipients.

Further, the present synergistic nutritional composition is useful for improving vascular endothelial function in a subject in need thereof.

BACKGROUND AND PRIOR ART

Endothelium refers to cells that line the interior surface of blood vessels and lymphatic vessels, forming an interface between circulating blood or lymph in the lumen and the rest of the vessel wall. It is a thin layer of simple, or single-layered, squamous cells called endothelial cells. Endothelial cells in direct contact with blood are called vascular endothelial cells, whereas those in direct contact with lymph are known as lymphatic endothelial cells.

The endothelial cells form a one-cell thick walled layer called endothelium that lines all the blood vessels such as arteries, arterioles, venules, veins and capillaries. Smooth muscle cells layer beneath the endothelial cells. The exception to this is the capillaries where endothelium makes up the entire blood vessel wall.

The endothelium is directly involved in peripheral vascular disease, stroke, heart disease, diabetes, insulin resistance, chronic kidney failure, tumor growth, metastasis, venous thrombosis, and severe viral infectious diseases.

The vascular system is a network of vessels that is distributed over the entire area of a living body.

Vascular endothelial cells (VECs) form a monolayer that lines the internal lumen of the blood vessels. This monolayer constitutes a physical barrier between blood and tissues and regulates the exchange of molecules between blood and tissues. Although it is a simple, single layer of cells, the vascular endothelium is considered an active organ that responds to and secretes chemical signals. The vascular endothelium regulates the passage of substances and cells from the blood to the tissues and is central to the regulation of vascular tone (the balance between blood vessel constriction and dilation).

VECs metabolize, synthesize and release a variety of substances, including vasoactive substances regulating vascular tone, blood pressure and local blood flow, such as vasodilators like nitric oxide (NO), prostacyclin, kinins, endothelium-derived hyperpolarizing factors (EDHF), the substances participating in coagulation, fibrinolysis and inflammatory and immunological reactions, vasoconstrictors such as endothelin-1 and PGH2, reactive oxygen species (ROS) and reactive nitrogen species (RNS) involved in oxidation and nitrosylation of proteins and lipids, and growth factors promoting cell growth.

Any disturbance affecting the capacity and equilibrium of the endothelium as a physical barrier and to metabolize, synthesize and release vasoactive substances will cause endothelial dysfunction, and contribute to the development and progression of cardiovascular diseases (CVDs). Dysfunction of the vascular endothelium is a hallmark of human diseases [*World J Cardiol*. 2015 Nov. 26; 7(11): 719-741].

Different risk factors such as hypercholesterolemia, homocystinemia, hyperglycemia, hypertension, smoking, inflammation, aging, chronic systemic infection, family history of premature atherosclerotic disease dysfunction, oxidative stress, increase of inhibitors of endogenous NO synthesis, inflammation, adipocytokines derived from visceral fat-obesity, increase of aldosterone and depletion of tetrahydrobiopterin (BH4) contribute to the development of endothelial dysfunction.

Endothelial dysfunction has been shown to be of significance in predicting stroke and heart attacks due to the inability of the arteries to dilate fully. This dysfunction may be a result of high blood pressure, diabetes, high cholesterol and smoking.

Endothelial cells regulate the amount of blood flow through the vascular system. The dysfunction of the endothelium gradually leads to loss of its responsiveness, which leads to a reduction of the amount of blood that flows through the body. Declining endothelial function is the process that underlies a major cause of cardiovascular diseases.

Among endothelium-derived vasodilators, NO occupies a central position because changes in the release of endothelial NO plays a crucial role in the disturbance of vascular homeostasis and in the development of endothelial dysfunction associated with various cardiovascular disorders.

According to the American Heart Association (AHA), an estimated more than 92.1 million American adults are living with some form of cardiovascular disease including hypertension, coronary artery disease, myocardial infarction, angina pectoris, stroke and heart failure or the after-effects of stroke. Most of the CVDs are the result of a dysfunctional endothelium and inability to produce NO and/or maintain NO homeostasis and signaling.

Hence there is need to increase or promote levels of NO for maintaining vascular homeostasis. When the vascular nitric oxide concentrations are increased, the arterial walls relax and allow increased blood flow and lowered blood pressure.

Some of the NO enhancing agents and activity for endothelial function thereof are described in the prior arts.

U.S. Pat. No. 9,833,426B2 discloses an agent for enhancing NO production, comprising citrulline or a salt thereof and serine or a salt thereof as an active ingredient, for preventing or ameliorating vascular endothelial malfunction.

JP2012041296A provides the vascular endothelial function improving agent obtained by formulating a polyphenol derived from grape which is extracted from dregs produced during production of wines with water, ethanol, or water-ethanol with L-arginine as active ingredients; nitric oxide production promoter; and food and drink.

JP2013227256A provides piceatannol as an active ingredient for improving vascular endothelial function by promoting the production of endothelial nitric oxide synthase (eNOS).

It is observed that, the production of NO from L-arginine by nitric oxide synthase (NOS) enzymes is one of the most complicated and complex reaction in the body involving a 5-electron oxidation with many cofactors and prosthetic groups. As a result, there are many steps in the pathway that may be affected and thereby ultimately lead to decreased NO production with poor half-life and bioavailability.

Intriguingly, the inorganic nitrate rich vegetables may play a major role in the cardiovascular health, presumably through enhancing NO bioavailability in the vasculature.

Nitrate/nitrite rich food in our diet influences cardiovascular system through increasing vascular NO bioavailability via the Nitrate-Nitrite-NO pathway. In this context, the use of supplementation with inorganic nitrate salts (eg: sodium nitrate, potassium nitrate) can improve NO bioavailability in the vasculature, presumably through its interaction with the vascular endothelium that leads to improved clinical outcome in cardiovascular disease subject.

Thus, nitrite is now recognized as a reservoir of NO-like bioactivity to be acted upon when enzymatic NO production from NOS is insufficient.

In addition to NO, other endothelial mediators are also found to be effective for improving vascular health due to their potent vasodilation activity.

Prostaglandins and thromboxane $A_2$ ($TXA_2$), collectively termed prostanoids, are formed when arachidonic acid (AA), is released from the plasma membrane by phospholipases (PLAs) and metabolized by the sequential actions of prostaglandin G/H synthase, or cyclooxygenase (COX), and respective synthases.

There are four principal bioactive prostaglandins generated in vivo: prostaglandin (PG) $E_2$ ($PGE_2$), prostacyclin ($PGI_2$), prostaglandin $D_2$ ($PGD_2$) and prostaglandin $F_{2\alpha}$ ($PGF_{2\alpha}$).

A significant amount of evidence has proven that prostacyclin or prostaglandin I2 ($PGI_2$), is one of the most important anti-platelet aggregation and vasodilation mediators, which plays a key role in the prevention and treatment of vascular and heart diseases. The most popular non-steroidal anti-inflammatory drugs (NSAIDs), which are commonly used for the prevention and treatment of inflammation, may reduce prostacyclin biosynthesis in cells through their inactivation of COX-1 and COX-2, which are the upstream enzymes required for prostacyclin production.

Prostacyclin is produced in endothelial cells, which line the walls of arteries and veins, from prostaglandin H2 (PGH2) by the action of the enzyme prostacyclin synthase.

It is an end product derived from the sequential metabolism of arachidonic acid via cyclooxygenase and PGI synthase (PGIS). $PGI_2$ is a potent vasodilator that prevents formation of platelet plug or hemostatic plug or platelet thrombus.

PGI2 is one of the most important prostanoids that regulates cardiovascular homeostasis. Vascular cells, including endothelial cells, vascular smooth muscle cells (VSMCs) and endothelial progenitor cells (EPCs), are the major source of PGI2.

It is observed that, pharmacological activation of SIRT1 may hold therapeutic promise for treatment of age-related endothelial dysfunction. A specific small-molecule activator of SIRT1, exerts beneficial effects to improve vascular health and increases lifespan of a subject, preferably human.

'SIRT1' also known as Sirtuin 1, which is a nicotinamide adenine dinucleotide (NAD)-dependent class III histone deacetylase (HDAC). SIRT1 removes acetyl groups from many non-histone proteins and is involved in a broad range of physiological functions; including the control of gene expression, metabolism, and aging. Increasing evidence has demonstrated the protective roles for SIRT1 in vascular biology and atherosclerosis. SIRT1 prevents hyperglycemia-induced endothelial cell dysfunction by repressing collagen homologue (p66Shc) expression [*Circ Res.* 2011 Sep. 2; 109(6): 639-48].

Further Chlopicki S et al. reported that 1-Methylnicotinamide (MNA), a primary metabolite of nicotinamide and one of the prominent SIRT1 activators, exerts anti-thrombotic activity mediated by a cyclooxygenase-2/prostacyclin pathway [*Br J Pharmacol.* 2007 September; 152(2): 230-9].

Endothelial function can be improved by lifestyle measures that are commonly encouraged on all of us to reduce our risk of cardiovascular disease, including weight loss, exercise, smoking cessation, control of hypertension, and control of diabetes.

Certain pharmacological risk-control measures are well documented to reduce endothelial dysfunction which include: use of calcium antagonist, beta blockers, Angiotensin-converting enzyme (ACE) inhibitors, statins, rennin inhibitors, insulin resistance improving drugs.

At this point, it is apparent that endothelial dysfunction is related to a reduction in the levels of vasodilators in blood vessel walls. A deficiency in vasoactive mediators production leads to excess constriction of blood vessels (which can produce hypertension), contributes to the activation of platelets (leading to blood clotting), increases the stimulation of inflammation in blood vessel walls, and increases the permeability of the vessel walls to damaging lipoproteins and various toxins. Hence there is need of potent bioactive agents that enhance the vasodilation activity of endothelial cells without any side effects.

Due to the differences in risk factors contributing to the different cardiovascular diseases and the differences in mechanisms of action, treatment of endothelial dysfunction with drugs needs to be carried out according to specific mechanisms underlying endothelial dysfunction of the disease.

Extensive research by present inventors has shown that vascular endothelial function can be improved with synergistic effect of vasodilators, wherein one moiety ameliorates production of NO, while other enhances levels of mediators responsible for inhibition of platelets aggregation i.e. prostanoid PGI2.

The present inventors have successfully developed synergistic composition of specific vasodilators enhancers or stimulators useful for improving vascular endothelial function via specific coupled pathway without any side effects.

Objective of the Invention

The primary object of the present invention is to provide nutritional composition for improving vascular endothelial function with high bioavailability of vasoactive substances that carries no side effects.

Another object of the present invention is to provide composition comprising of potent nutrients that yield synergistic effect of vasodilation by enhancing NO production and concomitantly or subsequently inhibiting platelets aggregation by enhancing PGI2 secretion.

Yet another object of the present invention is to provide synergistic nutritional composition for improving endothelial dysfunction in a subject in need thereof, particularly endothelial dysfunction related to cardiovascular diseases (CVD).

Another object of the present invention is to provide cost effective, non-toxic, environmentally friendly, dietary supplement for treating endothelial dysfunction without any adverse effect.

SUMMARY OF THE INVENTION

To meet the above objects, the inventors of the instant invention carried out thorough experiments to establish the significant effect of vasoactive mediators' enhancers that improve vascular health in a subject.

In one aspect, the invention relates to synergistic composition of active nutrients for treating endothelial dysfunction.

In another aspect, the invention relates to synergistic composition of vasoactive mediators like prostanoids and nitric oxide and enhancing agents thereof for improving vascular endothelial function.

In yet another aspect, the invention provides potent synergistic composition comprising combination of vasoactive prostanoids enhancing agent and nitric oxide enhancer in an effective amount, wherein vasoactive prostanoid i.e. prostacyclin or prostaglandin I2 (PGI2) enhancing agent is 'N-1-methyl nicotinamide salt' and nitric oxide enhancer is 'inorganic nitrate/nitrite extracted from natural source, along with pharmaceutically acceptable excipients.

In yet another aspect, the instant invention provides synergistic compositions comprising combination of N-1-methyl nicotinamide salt and standardized red spinach extract enriched with inorganic nitrate for treating a subject suffering from endothelial dysfunction.

In further aspect, the invention relates to synergistic nutritional compositions comprising combination of N-1-methyl nicotinamide salt which is present in the range of 1 to 500 mg and standardized red spinach extract enriched with inorganic nitrate content present in the range of 10-500 mg, wherein inorganic nitrate of standardized red spinach extract is present in the range of 1 to 100 mg, along with pharmaceutically acceptable excipients/carriers.

In yet another aspect, the invention relates to synergistic nutritional composition of N-1-methyl nicotinamide and standardized red spinach extract enriched with inorganic nitrate content, wherein the N-1-methyl nicotinamide inhibits platelets aggregation and inorganic nitrate/nitrite regulates vascular tone and thereby improving vascular health in a subject in need thereof.

Further, the present synergistic composition is useful for improving vascular endothelial function via specific coupled pathway, wherein prostacyclin and nitric oxide are mediated by cyclic nucleotides, i.e. cyclic adenosine monophosphate (cAMP) and cyclic guanosine monophosphate (cGMP) respectively, leading to improved vascular health.

Abbreviations cAMP: Cyclic adenosine monophosphate
cGMP: Cyclic guanosine monophosphate
NO: Nitric oxide
SIRT1: Silent information regulator Ti (sirtuin family)
1-MNA: N-1-methyl nicotinamide
PGI2: Prostaglandin I2 (Prostacyclin)
COX-1: Cyclooxygenase-1 (isoform 1 of cyclooxygenase)
COX-2: Cyclooxygenase-2 (isoform 2 of cyclooxygenase)
EDD: Endothelium-dependent dilation
CVDs: Cardiovascular diseases
VECs: Vascular endothelial cells
RT-PCR: Reverse transcription-polymerase chain reaction
GAPDH: Glyceraldehyde 3-phosphate dehydrogenase
TAE: Tris-acetate-EDTA buffer
EDTA: Ethylenediaminetetraacetic acid
eNOS: endothelial nitric oxide synthase

DETAILED DESCRIPTION OF THE INVENTION

Figure 1:
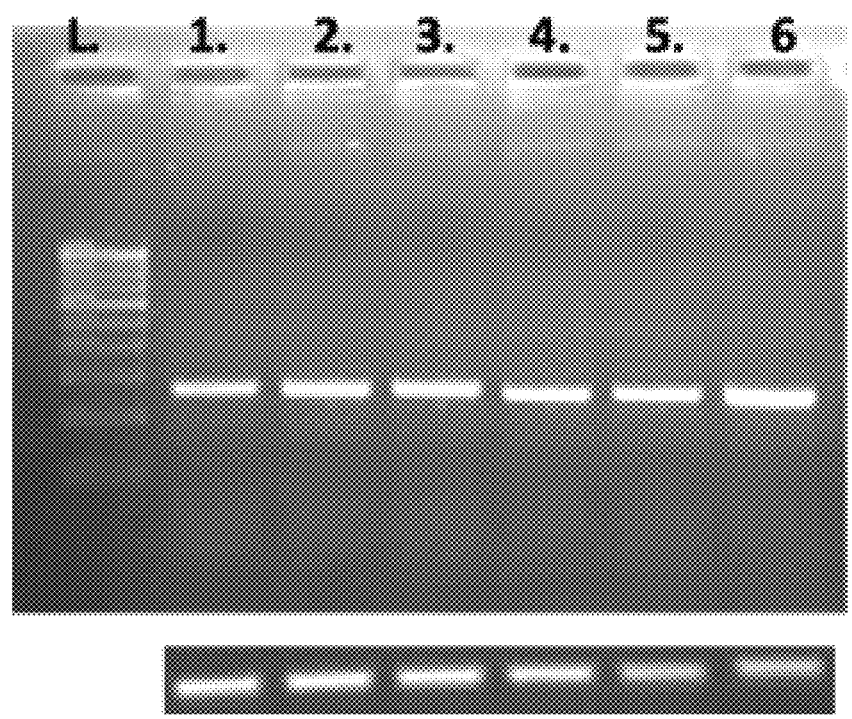
FIG. 1 depicts semi-quantitative RT-PCR profile of $PGI_2$ gene amplified in H9C2 with G1, G2 and G3, where L=100 bp Ladder, 1=cell control, 2=Nitroglycerin (250 µg/ml), 3=G1(500 µg/ml), 4=G2(500 µg/ml), 5=G3(500 µg/ml), 6=TNF alpha treated cells.
Figure 2:
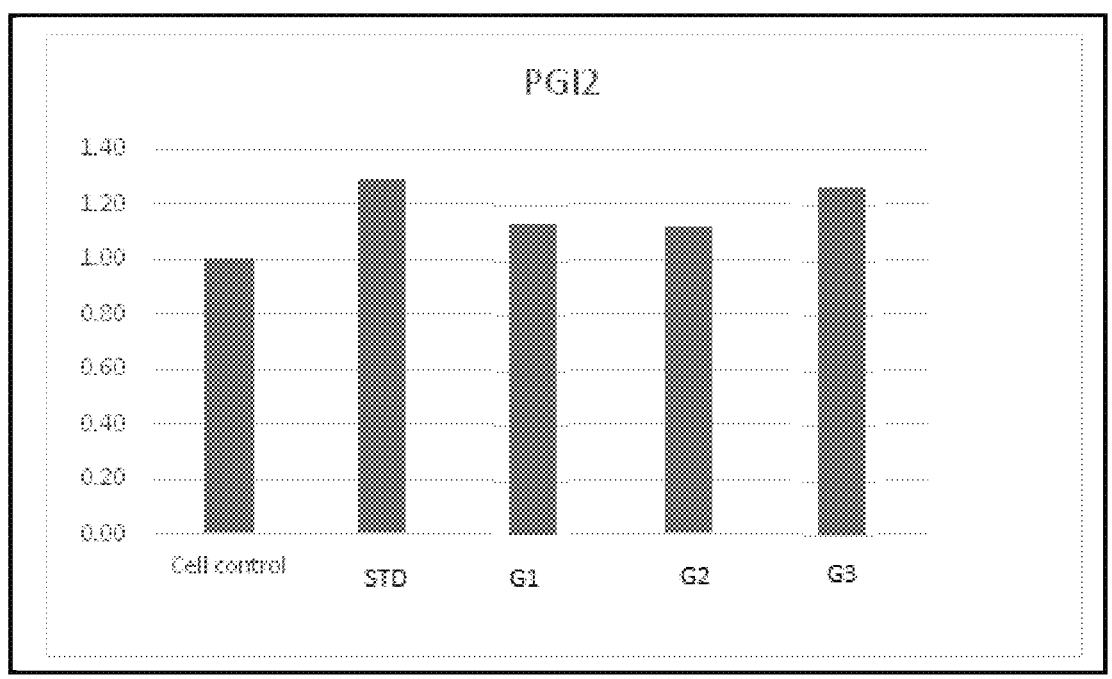
FIG. 2 depicts semi quantitative densitometric analysis of gene transcripts from G1, G2, G3 treated cells; the relative level of $PGI_2$ gene expression is normalized to GAPDH.
Figure 3:
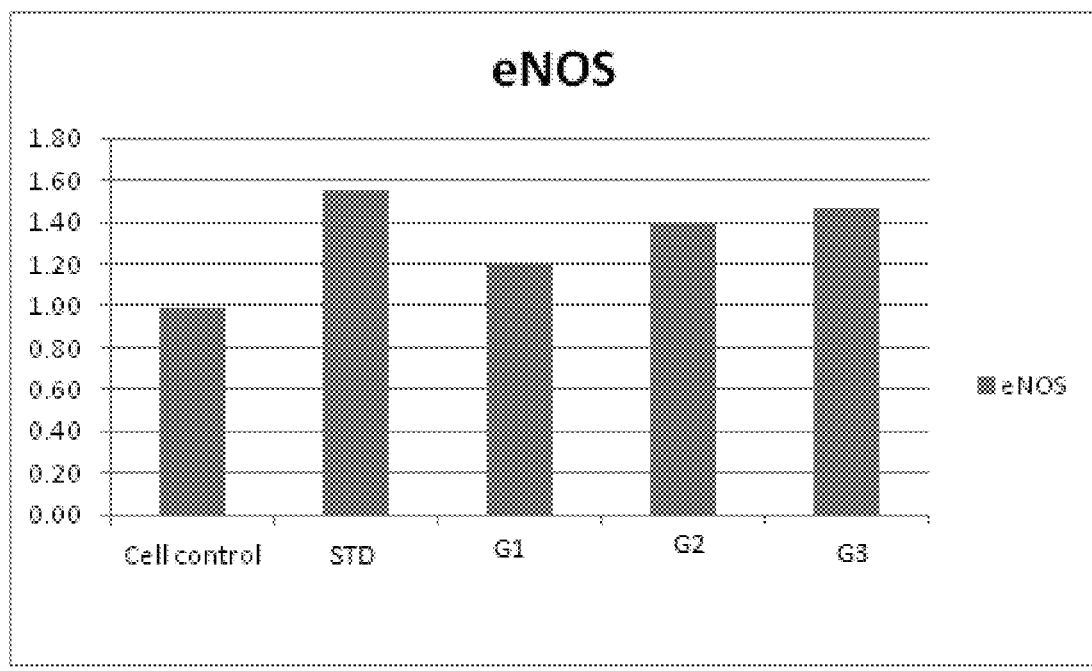
FIG. 3 depicts Semi quantitative densitometric analysis of gene transcripts from G1, G2, G3 treated cells; the relative level of eNOS gene expression is normalized to β-Actin.

The invention will now be described in detail in connection with certain preferred and optional embodiments, so that various aspects thereof may be more fully interpreted and comprehended. However, any skilled person or artisan will appreciate the extent to which such embodiments could be generalized in practice.

It is further to be understood that all terminology used herein is for the purpose of describing particular embodiments only, and is not intended to be limiting in any manner or scope.

Unless defined otherwise, all technical and scientific expressions used herein have the same meaning as commonly understood by one of ordinary skill in the art to which embodiments of the invention pertain.

In describing and claiming the embodiments of the present invention, the following terminology will be used in accordance with the definitions set out below, that can be easily perceived by artisan.

The singular forms "a," "an," and "the" include plural reference unless the context clearly dictates otherwise.

The term "pharmaceutically/nutraceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Particularly the term "pharmaceutically-acceptable salts" refers to the relatively non-toxic, inorganic and organic acid addition salts of compounds, as well as solvates, co-crystals, polymorphs and the like of the salts.

The term 'nutritional composition' does not limit the scope of the invention only for nutrients but it also includes food supplements, dietary supplements, plant extract, herbal products which are resourced from natural products that eventually contribute to therapeutic effect in a subject.

The 'vasoactive mediators' can also be referred as vasodilators, vasoactive agents, vasoactive substances, endothelial relaxing factors and likewise. The term "vasoactive mediators" is defined as mediators synthesized or secreted by vascular endothelial cells, that help to keep the surface of the normal endothelium non-thrombogenic. The vascular endothelium regulates the tone of the underlying smooth muscle and the reactivity of blood elements such as platelets and neutrophils by the release of mediators, in particular nitric oxide, prostacyclin and endothelin-1. The first two of these are potent vasodilators which also inhibit platelet and neutrophil aggregation and adhesion, while endothelin-1 is the most potent mammalian vasoconstrictor peptide.

In the present invention 'vasoactive mediators' are particularly 'vasodilators' composed of NO and prostacyclin in specific ratio.

In preferred embodiment, the invention relates to synergistic nutritional composition of vasoactive mediators enhancers, wherein the vasoactive mediators are 'vasodilators' preferably containing prostacyclin (PGI2) and nitric oxide (NO).

In another embodiment, the invention provides a potent synergistic nutritional composition(s) for treating endothelial dysfunction in a subject in need thereof, wherein the composition comprises an exogenous blend of vasoactive mediators enhancers along with pharmaceutically acceptable excipients; wherein the vasoactive mediators are prostaglandin I2 (PGI2) and nitric oxide.

The synergistic composition comprises combination of prostacyclin (PGI2) enhancing agent and nitric oxide enhancer, in an effective amount, wherein prostacyclin (PGI2) enhancing agent is N-1-methyl nicotinamide and nitric oxide (NO) enhancing agent is inorganic nitrate/nitrite extracted from natural source.

In another embodiment, the invention provides a potent synergistic nutritional composition wherein the (PGI2) enhancer is N-1 methyl nicotinamide salt; and nitric oxide enhancer is standardized red spinach extract enriched with nitrate content.

In another preferred embodiment, the invention provides nutritional composition comprising combination of N-1-methyl nicotinamide and inorganic nitrate/nitrite, which act synergistically through coupled mechanism, wherein N-1-methyl nicotinamide stimulates prostacyclin level, where PGI2 inhibits platelet aggregation by increasing cyclic adenosine monophosphate (cAMP) level; concurrently NO production is increased by inorganic nitrate/nitrite that regulates blood vessel relaxation by increasing cyclic guanosine monophosphate (cGMP) level, thus the smooth functioning of vascular system is maintained.

In another embodiment, the invention discloses vasoactive mediators' enhancers; wherein the enhancers preferably induce the secretion of vasodilators i.e. prostacyclin and nitric oxide. Particularly prostacyclin (PGI2) enhancing agent is N-1-methyl nicotinamide and nitric oxide (NO) enhancer is inorganic nitrate/nitrite, which are employed in therapeutically effective amount.

In another embodiment, the PGI2 level is stimulated by SIRT1 activator, preferably SIRT1 activator is 1-methyl nicotinamide. It is a potent vasoactive prostanoid enhancer or activator for increasing endothelial secretion of prostacyclin (PGI2).

In one embodiment, the present invention provides SIRT1 activator for increasing endothelial secretion of prostacyclin (PGI2), wherein the SIRT activator is 'N-1-methyl nicotinamide' ($N^1$-MNA) salt.

1-MNA can also be referred as 1-Methyl-3-carbamoylpyridinium cation; 1-Methylnicotinamide; 3-Amido-N-methylpyridinium: 1-methyl-3-Pyridinecarboxamide; 3-carbamoyl-1-methyl-Pyridinium; 1-methyl nicotinamide; N-1-methylnicotinamide; N-Methyl-3-carbamidopyridinium; N-Methyl-3-carbamoylpyridinium ion; N'-methylnicotinamide; N'methylnicotinamide; N1-Methylnicotinamide; Trigonellinamide; 1-Methylnicotinamide cation. Herein after 1-MNA is referred as '$N^1$ MNA'.

The salts of 1-MNA are selected from the group consisting of N(1)-methylnicotinamide chloride; N(1)-methylnicotinamide cyanide; N(1)-methylnicotinamide fluoride; N(1) methylnicotinamide iodide, N(1)-methylnicotinamide methyl sulfate; N(1)-methylnicotinamide perchlorate; N(1)-methylnicotinamide bromide; N(1)-methylnicotinamide iodide; N(1)-methylnicotinamide tetrafluoroborate (1); trigonellamide chloride; particularly the $N^2$ MNA salt is chloride.

It may be noted that $N^1$-MNA is produced from nicotinamide in a process of nicotinamide methylation. The main food sources of nicotinamide and nicotinic acid are meat, poultry, liver, fish, eggs, $N^1$-MNA nuts, rice bran and wheat bran. Significant amounts of nicotinamide can also be obtained from legumes, nuts, mushrooms and sunflower seeds (*EFSA Journal* 2017; 15(10):5001).

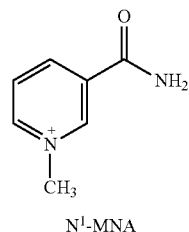

$N^1$-MNA

In another embodiment, SIRT1 activation by $N^1$-MNA improves endothelium-dependent dilation (EDD) in a subject by enhancing the production of COX-2 vasodilators. Endothelial COX-2 production of vasodilators can act as a compensatory mechanism to maintain EDD in settings of impaired NO-mediated dilation. Further be noted that induction of COX-2 in the endothelium would result in increased synthesis of PGI2.

In another embodiment, the invention provides effective amount of $N^1$-MNA that stimulates the release of (PGI2) from endothelial cells.

Notably, the activation of prostanoid receptors (IP receptors) by PGI2 activates adenylate cyclase to synthesize cyclic adenosine monophosphate (cAMP) from adenosine triphosphate (ATP), causing vascular smooth muscle relaxation or vasodilation.

Further $N^1$-MNA induces prostacyclin formation which inhibits platelet aggregation by increasing cyclic AMP levels. Prostacyclin is a circulating hormone continually released by the lungs into the arterial circulation. Circulating platelets are, therefore, subjected constantly to prostacyclin stimulation and it is via this mechanism that platelet aggregability in vivo is controlled.

In another embodiment, the synergistic composition comprises therapeutically effective amount of $N^1$-MNA or pharmaceutically acceptable salts thereof, wherein $N^1$-MNA is present in the range of 1-500 mg, preferably in the range of 1-250 mg of total composition.

In another preferred embodiment, the invention provides synergistic nutritional composition, wherein the nitric oxide (NO) enhancer is nitrate/nitrite, preferably inorganic nitrate extracted from natural source.

Particularly, nitrate-nitrite-NO pathway, in which endogenous nitrate undergoes reduction to nitrite and then to NO in various tissues including blood, with bioactive NO production in the body. The released NO activates soluble guanylate cyclase, leading to the conversion of guanosine triphosphate (GTP) into cyclic guanosine monophosphate (cGMP) that causes vascular smooth muscle relaxation.

Moreover, NO exerts anti-inflammatory, antiplatelet, antiproliferative and antimigration actions that contribute to the maintenance of an adequate environment for the endothelium.

Apparently endothelial NO production is oxygen-dependent, indicating that endothelial NO-driven processes decline with depletion of normal oxygen levels. In addition, cardiovascular diseases share a common pathophysiology involving depletion of normal oxygen levels, coupled to diminished blood supply due to atherosclerosis (i.e., thickening or narrowing of the arteries due to the development of plaques in the arterial wall) and/or thrombosis (i.e., arterial blood clotting); for example, thickening of coronary arteries can restrict blood supply to myocardium leading to myocardial infarction or acute heart attack.

Moreover, NO production from nitrate-nitrite-NO pathway increases with decrease in oxygen. In this regard, it is demonstrated that NO generation from the nitrate-nitrite-NO pathway may contribute to hypoxic vasodilation.

Lundberg, Jon O., et al. reports that food enriched with inorganic nitrate is a potential source for systemic generation of nitric oxide (*Free Radical Biol Med.* 2004, vol. 37, p. 395-400).

There are two known pathways for NO production in the human body. The first is the endogenous pathway, where 1-arginine is converted to NO by nitric oxide synthases (NOS).

The second pathway is the exogenous pathway, which comprises consumption of nitrate rich food.

After ingestion of nitrate rich vegetables, ($NO_3^-$) nitrate gets absorbed into circulation, undergoes reduction to nitrite ($NO_2^-$) and then to nitric oxide (NO) this nitric oxide formation supports vasodilation. This pathway is also known as $NO_3^-$—$NO_2$—NO reduction pathway.

In another embodiment, the vegetables enriched with inorganic nitrate can be selected from Class I, Class II, Class III, Class IV and Class V; preferably the inorganic nitrate is sourced from Class V vegetables such as red beetroot, red spinach and like thereof.

The classification of vegetables according to inorganic nitrate content (mg/100 gm fresh weight) is given in Table 1 as below:

TABLE 1

| | |
|---|---|
| Class I (<20) | Artichoke, asparagus, broad bean, Brussels sprouts, eggplant, garlic, onion, green bean, mushroom, peas, pepper, potato, squash, tomato |
| Class II (20 to <50) | Broccoli, carrot, cauliflower, cucumber, pumpkin, chicory |
| Class III (50 to <100) | Cabbage, dill, turnip, Savoy cabbage |
| Class IV (100 to <250) | Celeriac, Chinese cabbage, endive, escarole, fennel, kohlrabi, leaf chicory, leek, parsley |
| Class V (>250) | Celery, chervil, cress, Lamb's lettuce, lettuce, radish, red beetroot, rocket (rucola), spinach, Swiss chard |

In yet another embodiment, the pharmaceutically acceptable compositions of the invention include, but are not limited to inorganic nitrite, e.g., a salt or ester of nitrous acid ($HNO_2$), or a pharmaceutically acceptable salt thereof. Nitrite salts can include, without limitation, salts of alkali metals, e.g., sodium, potassium; salts of alkaline earth metals, e.g., calcium, magnesium, and barium; and salts of organic bases, e.g., amine bases and inorganic bases.

In another embodiment, the invention discloses that sodium nitrite may potentially be useful for improving endothelial function and correcting vascular NO deficiency.

In addition to sodium nitrite, representative inorganic nitrite compounds include: ammonium nitrite ($NH_4NO_2$), barium nitrite ($Ba(NO_2)_2$; e.g., anhydrous barium nitrite or barium nitrite monohydrate), calcium nitrite ($Ca(NO_2)_2$; e.g., anhydrous calcium nitrite or calcium nitrite monohydrate), cesium nitrite ($CsNO_2$), cobalt(II)nitrite ($Co(NO_2)_2$), cobalt(III)potassium nitrite ($CoK_3(NO_2)_6$; e.g., cobalt(III) potassium nitrite sesquihydrate), lithium nitrite ($LiNO_2$; e.g., anhydrous lithium nitrite or lithium nitrite monohydrate), magnesium nitrite ($MgNO_2$; e.g., magnesium nitrite trihydrate), potassium nitrite ($KNO_2$), rubidium nitrite ($RbNO_2$), silver(I)nitrite ($AgNO_2$), strontium nitrite ($Sr(NO_2)_2$), and zinc nitrite ($Zn(NO_2)_2$).

It may be noted that nitric oxide (NO) is an endothelium-derived relaxation factor which regulates multiple biological processes including the control of the vascular tone, cardiac and vascular remodeling, and vascular smooth muscle cell proliferation.

Further nitric oxide mediates essential vascular homoeostasis, including vasodilation, and antiplatelet activity, and affects several growth factors involved in endothelial homoeostasis.

In another embodiment, the invention provides synergistic effect of vasodilators, wherein NO production is achieved through exogenous pathway.

The reduced NO enters vascular smooth muscle cells, where it increases cyclic guanosine 3',5'-monophosphate (cGMP) production by activating soluble guanylyl cyclase enzyme, leading to smooth muscle relaxation (vasodilation).

The nitrate/nitrite compounds of the present invention can be prepared in a variety of ways known to one of ordinary skill in the art of chemical synthesis. Methods for preparing nitrite salts are well known in the art and a wide range of precursors and nitrite salts are readily available commercially.

In another embodiment, the synergistic composition comprises therapeutically effective amount of inorganic nitrate or nitrite salts, wherein inorganic nitrate or nitrite either alone or in combination may be present in the range of 1-100 mg, preferably in the range of 1-80 mg of total composition.

In yet another embodiment, the invention provides nutritional composition of prostacyclin enhancing agent and nitric oxide enhancer for improving endothelial function.

The composition exhibits synergistic effect, wherein $N^1$-MNA induces prostacyclin formation which inhibits platelet aggregation by increasing (cAMP) levels and inorganic nitrate or nitrite increases smooth muscle relaxation (vasodilation) by augmenting (cGMP) production.

More particularly prostacyclin ($PGI_2$) activates cell surface prostaglandin I2 receptors linked to activation of adenylate cyclase (AC), leading to the conversion of ATP to cAMP. Nitric oxide freely enters cells, where it activates soluble guanylyl cyclase (GC), which converts GTP to cGMP. Activation of AC or GC and the subsequent increase in cAMP and cGMP respectively, results in inhibition of platelet activation and vasodilatation.

Prostacyclin is responsible mainly for maintaining vascular thromboresistance against platelet clumps, inhibits proliferation of vascular smooth muscle and modulates cholesterol turnover, and nitric oxide controls vascular tone and structure.

Moreover, prostacyclin and nitric oxide synergize in their antiplatelet, and cardioprotective vasodilation actions.

In subsequent embodiment, the invention provides method for evaluating the endothelial dysfunction in subject, wherein the method includes invasive methods by using quantitative angiography and intracoronary Doppler wire within coronary circulation and non-invasive methods, including venous occlusion plethysmography to measure forearm blood flow, flow-mediated dilatation (FMD) in brachial artery, and peripheral arterial tonometry measuring pulsatile volume changes in the distal digit.

In yet another preferred embodiment, the invention relates to synergistic nutritional compositions comprising combination of $N^1$-MNA present in the range of 1 to 500 mg and inorganic nitrate/nitrite present in the range of 1 to 100 mg along with pharmaceutically acceptable excipients/carriers.

Particularly, the invention relates to synergistic nutritional compositions comprising combination of $N^1$-MNA which is present in the range of 1 to 250 mg and inorganic nitrate/nitrite present in the range of 1 to 80 mg, along with pharmaceutically acceptable excipients/carriers.

In some embodiment, the invention provides value added inorganic nitrate obtained from natural source; particularly nitrate is obtained from standardized red spinach (*Amaranthus*) extract. The nitrate content is not less than 9.0%.

The term 'standardized' refers to the value added product where nitrate content is enriched with the process under generally acceptable guidelines for standard substances.

In yet another embodiment, the invention provides standardized red spinach extract which is present in the range of 10 to 500 mg, preferably 50 to 300 mg, wherein the extract contains inorganic nitrate in the range of 1 to 100 mg, preferably 5-50 mg of total extract.

Red spinach is a member of the plant family Amaranthaceae, which includes nearly 2,500 species ranging from spinach to beetroot to grains such as amaranth and *quinoa*. The *Amaranthus* genus comprising species such as *Amaranthus caudatus, Amaranthus cruentus, Amaranthus tricolor, Amaranthus blitum, Amaranthus viridis, Amaranthus dubius, Amaranthus hypochondriacus, Amaranthus hybridus* or like thereof.

In the present invention the preferable *Amaranthus* species is *Amaranthus cruentus*; wherein the leaves of the plants are extracted by known method to get extract with enriched nitrate content (not less than 9.0%); preferably containing 9.24% of nitrate on dried basis.

'*Amaranthus cruentus*' has several common names, including blood amaranth, red amaranth, purple amaranth, prince's feather, Mexican grain amaranth, Amaranth, African spinach, Indian spinach. For present composition the specific breed of *Amaranthus cruentus* is developed and cultivated in the territory of India.

In further embodiment, the invention provides the nutrition composition comprising standardized red spinach (*Amaranthus*) extract containing more than 9.0% of nitrate; preferably 9.0% to 12.0%, more preferably 9.10 to 9.80%.

In some embodiment the invention provides the nutrition composition comprising standardized red spinach (*Amaranthus*) extract containing 9.24% of inorganic nitrate content.

In one more embodiment, the invention offers nutritional composition comprising synergistic exogenous blend or combination of $N^1$-methyl nicotinamide chloride and standardized red spinach extract enriched with nitrate content, which gives significant improvement in vascular endothelial function without any adverse or side effects.

In one preferred embodiment, the invention provides synergistic nutritional composition for ameliorating vascular endothelial function which comprises combination of $N^1$-methyl nicotinamide chloride ($N^1$-MNA) chloride and standardized red spinach extract enriched with nitrate content, wherein the $N^1$-methyl nicotinamide chloride and the standardized red spinach extract enriched with nitrate content are present in the ratio of 1:0.5 to 1:8, particularly in the ratio of 1:1 to 1:6 along with pharmaceutically acceptable excipients.

Moreover, the composition comprising synergistic exogenous blend of $N^1$-MNA chloride and standardized red spinach extract enriched with nitrate content, wherein nitrate content is not less than 9.0%, particularly 9.0% to 12.0% by weight of the standardized red spinach extract.

In yet another embodiment, the invention provides synergistic nutritional composition, comprising $N^1$-MNA chloride and nitrate of standardized red spinach extract, which are present in the ratio of 1:0.1 to 1:1; preferably in the ratio of 1:0.1 to 1:0.6.

In another embodiment, the composition comprising chloride salt of $N^1$-MNA, and is present in the range of 5-50% by weight of total composition.

In yet another embodiment, the composition comprising standardized red spinach extract enriched with nitrate content, preferably red spinach extract is *Amaranthus cruentus* extract, present in the range of 30-90% by weight of total composition.

The *Amaranthus cruentus* dried leaves are treated with solvent and dried by conventional method to get value added nitrate enriched powder. Particularly it is an aqueous extract of *Amaranthus cruentus* dried leaves.

In further embodiment, the composition comprising standardized red spinach extract is enriched with nitrate content; wherein the nitrate content is 9.0-12.0% by weight of total standardized red spinach extract and 2.0 to 10.0% by weight of total composition.

In another embodiment, the red spinach (*Amaranthus cruentus* dried leaves) extract enriched with nitrate content comprises either inorganic or organic or a mixture thereof, preferably the red spinach (*Amaranthus cruentus*) extract is enriched with inorganic nitrate.

In another embodiment, the invention relates to synergistic nutritional composition which is useful for improving vascular endothelial function, particularly cardiovascular and metabolic diseases such as atherosclerosis, unstable angina, acute myocardial infarction, hypercholesterolemia, atherosclerosis, hypertension, congestive heart failure, restenosis, and cardiac transplantation.

In one preferred embodiment, the invention provides method of treating vascular endothelial dysfunction in a subject in need thereof, wherein the method comprises, administering to the subject a therapeutically effective amount of nutritional composition comprising exogenous synergistic blend of $N^1$-MNA chloride and standardized red spinach extract enriched with nitrate content, wherein the $N^1$-MNA chloride and the standardized red spinach extract are present in the ratio of 1:0.5 to 1:8 along with pharmaceutically acceptable excipients.

In another preferred embodiment, the invention provides a method of treating vascular endothelial dysfunction in a subject in need thereof, wherein the method comprises, oral administration of therapeutically effective amount of a nutritional composition comprising exogenous synergistic blend of $N^1$-MNA chloride and standardized red spinach extract enriched with nitrate content, wherein the $N^1$-MNA chloride and the standardized red spinach extract enriched with nitrate content are present in the ratio of 1:0.5 to 1:8; and the $N^1$-MNA chloride and nitrate of standardized red spinach extract are present in the ratio of 1:0.1 to 1:1, along with pharmaceutically acceptable excipients.

In another preferred embodiment, the invention provides method of treating neuropathic pain in a subject in need thereof, wherein the method comprising, administering to the subject a therapeutically effective amount of nutritional composition comprising exogenous synergistic blend of $N^1$-MNA chloride and standardized red spinach extract enriched with nitrate content, wherein the $N^1$-MNA chloride and the standardized red spinach extract are present in the ratio of 1:1 to 1:6 and the $N^1$-MNA chloride and the nitrate of standardized red spinach extract are present in the ratio of 1:0.1 to 1:0.6, along with pharmaceutically acceptable excipients.

It is noteworthy that present synergistic composition not only inhibits platelet aggregation by enhancing PGI2 expression but also improves functioning of neurons by activating eNOS expression.

In some embodiment, the present nutritional composition enriched with inorganic nitrate content ameliorates eNOS expression in microvascular endothelial cells.

In another embodiment, the invention provides synergistic nutritional composition of vasoactive mediators enhancers for improving vascular endothelial function or for treating endothelial dysfunction.

The condition relates to endothelial dysfunction including but not limited to arteriosclerosis, chronic kidney disease (CKD), high blood pressure, lipid metabolism, diabetes, ulcer, obesity, metabolic syndrome, coronary artery disease, cerebrovascular disease, disseminated intravascular coagulation syndrome (DIC), aortic diseases, cardiovascular dysfunction, including coronary artery disease (CAD), hypertension, microvascular angina, diastolic dysfunction, peripheral vascular disease (PAD), thrombosis, stroke, and dyslipidemia.

In another embodiment, endothelial dysfunction particularly relates to cardiovascular diseases which includes but is not limited to coronary heart disease—disease of the blood vessels supplying the heart muscle; cerebrovascular disease—disease of the blood vessels supplying the brain; peripheral arterial disease—disease of blood vessels supplying the arms and legs; rheumatic heart disease—damage to the heart muscle and heart valves from rheumatic fever, caused by streptococcal bacteria; congenital heart disease—malformations of heart structure existing at birth; deep vein thrombosis and pulmonary embolism—blood clots in the leg veins, which can dislodge and move to the heart and lungs.

In yet another embodiment, the invention relates to synergistic nutritional composition, which is useful for treating conditions related to endothelial dysfunction comprising the group consisting of arteriosclerosis, chronic kidney disease (CKD), high blood pressure, lipid metabolism, diabetes, ulcer, obesity, metabolic syndrome, coronary artery disease, cerebrovascular disease, disseminated intravascular coagulation syndrome (DIC), aortic diseases, cardiovascular dysfunction, including coronary artery disease (CAD), hypertension, microvascular angina, diastolic dysfunction, peripheral vascular disease (PAD), thrombosis, stroke, dyslipidemia, chronic diabetic ulcer, venous stasis ulcer, decubitus ulcer, steroid-dependent ulcer, chronic venous insufficiency, sickle cell disease, trauma, chronic non-healing burn injury, chronic non-healing surgical wound, chronic osteomyelitis, erectile dysfunction, postmenopausal state, preeclampsia, cigarette smoking, acute respiratory distress syndrome (ARDS), radiation injury, spinal cord injury, malnutrition, sepsis, chronic soft tissue infection, vitamin deficiency, osteoporosis, post-operative surgical wound, and old age.

In some embodiment, the oral administration of the effective dose of the composition is used for treating myocardial ischemia/infarction condition in human.

An "effective amount of nutrients" is an amount sufficient to prevent, treat, reduce, and/or ameliorate the symptoms and/or underlying causes of endothelial dysfunction.

In the context of the present invention, the term "treatment" and the like refer to alleviate, slow the progression, prophylaxis, attenuation, or cure the conditions related to endothelial dysfunction. The instant composition is used for treating endothelial dysfunction in a subject in need thereof, means either the administration of the remedy to prevent the onset or occurrence of endothelial dysfunction, or treat ongoing cause of endothelial dysfunction.

The 'subject in need thereof' pertains to subject, preferably mammal, more preferably human suffering from conditions related to endothelial dysfunction or in a subject to prevent occurrence of endothelial dysfunction.

The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art.

Thus, a "therapeutically effective amount" is an amount that reduces the risk, potential, possibility or occurrence of a disease or disorder, or provides some alleviation, mitigation, and/or reduction of at least one indicator (e.g., blood or serum CRP level), and/or decrease in at least one clinical symptom of a disease or disorder (e.g., endothelial dysfunction such as CVDs as disclosed herein).

A "pharmaceutically acceptable excipient," as used herein, refers any ingredient other than the compounds described herein (for example, a vehicle capable of suspending or dissolving the active compound) and having the properties of being nontoxic and non-inflammatory in a patient.

As used herein, the term "pharmaceutically acceptable carriers/vehicles/diluents or excipients" is intended to mean, without limitation, any adjuvant, carriers, excipients, binder, sweetening agent, diluent, preservative, dye/colorants, flavor enhancer, surfactant, wetting agent, dispersing agent, suspending agent, complexing agent, stabilizer, lubricant, isotonic agent, solvent, emulsifier, encapsulating agent, polymer, coating agent, wax, encapsulating polymeric delivery systems, antiadherent, antioxidant, pH-modifier, solvents, coatings, compression aids, disintegrant, emollient, fillers (diluents), film formers, fragrances, glidant (flow enhancers), lubricant, preservative, sorbent, anticaking agent, food additive, or waters of hydration.

In some embodiment of the invention, the diluents are selected from starches, hydrolyzed starches, and partially pregelatinized starches, anhydrous lactose, cellulose powder, lactose monohydrate, and sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulfate, cellulose acetate, corn starch, pregelatinized starch, dextrin, O-cyclodextrin, dextrates, dextrose, erythritol, ethylcellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

The amount of diluent in the pharmaceutical composition/formulation is present in the range of 1% to 30% by wt. of the total composition/formulation.

In further embodiment, the binder is selected from disaccharides such as sucrose, lactose, polysaccharides and their derivatives like starches, cellulose or modified cellulose such as microcrystalline cellulose and cellulose ethers such as hydroxypropyl cellulose (HPC); hydroxypropyl methyl cellulose (HPMC); sugar alcohols such as xylitol, sorbitol or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, copovidone, corn starch, pregelatinized starch, cottonseed oil, dextrates, dextrin, dextrose, ethylcellulose, guar gum, hydrogenated vegetable oil, mineral oil, hydroxyethyl cellulose, hydroxymethyl cellulose hydroxyl ethylmethyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methyl-cellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colourants and wax. The amount of binder in the pharmaceutical composition/formulation is present in the range of 0.5% to 20% by wt. of the composition/formulation.

In some embodiment, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulfate, medium-chain triglycerides, mineral oil, myristic acid, palmitic acid, poloxamer, polyethylene glycol, sodium benzoate, sodium chloride, sodium lauryl sulfate, sodium stearyl fumarate, stearic acid, talc, potassium benzoate or the like. The amount of lubricant in the pharmaceutical composition/formulation is present in the range of 0.1% by wt. to 5% by wt. of the total composition/formulation.

In some embodiment, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, magnesium silicate, magnesium trisilicate, silicon dioxide or the like. The amount of glidant present in the pharmaceutical composition/formulation ranges from 0.1% by wt. to 5% by wt. of the total composition/formulation.

In some embodiment, the solvent is selected from water, alcohol, isopropyl alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof. The amount of solvent in the pharmaceutical composition/formulation is used in a quantity sufficient to 100% by wt. of the composition/formulation.

The additional additives include polymer, a plasticizer, a sweetener, and a powdered flavor, preservative, colorant, surfactant and other excipients. The powdered flavor composition includes a flavoring associated with a solid carrier, coating materials are used, for example synthetic polymers, shellac, corn protein zein or other polysaccharides, gelatin, fatty acids, waxes, shellac, plastics, and plant fibers and like thereof. The additives are used in the range of 0.5 to 20% w/w of unit dose.

Further the surfactant is selected from anionic surfactants such as Sulfate, sulfonate, and phosphate esters or cationic surfactants such as quaternary ammonium salts, benzalkonium chloride or zwitterionic surfactants or non-ionic surfactants or fatty acid esters or biosurfactants or mixtures thereof, which are present in the range of 0.1 to 5% w/w of unit dose.

Notably, the instant synergistic nutritional composition is non-hazardous, non-toxic and safe for human consumption without any side effects, therefore the instant composition can also be used under preventive therapy in healthy subjects.

The present nutritional composition is used for improving vascular tone in the subject in need thereof, means the administration of the remedy either to prevent occurrence or for pre-existing cause of endothelial dysfunction.

In another embodiment, the invention provides a method of treating a subject suffering with endothelial dysfunction such as cardiovascular diseases, the method comprising administering to the subject an effective amount of the present synergistic nutritional composition to improve vascular tone The term "endothelial dysfunction" encompasses dysregulation of mechanistic processes. These processes include the control of vascular wall inflammation and smooth muscle proliferation, regulation of platelet adhesion, and aggregation, as well as modulation of thrombosis and fibrinolysis.

In some embodiment, the invention provides synergistic nutritional composition that improves endothelial function which includes regulation of endothelium-dependent vascular tone, endothelium-dependent vasoreactivity, endothelial vasomotor function and endothelial expression of inflammatory markers, endothelial repair and maintenance of vascular homeostasis.

The 'subject in need thereof' pertains to subject preferably mammal, more preferably human having pre-existing or onset symptoms of endothelial dysfunction.

The subject may be healthy person which can use the composition under preventive therapy.

The term "pharmaceutical composition," as used herein, represents a composition containing a compound described herein (e.g., inorganic nitrite, or any pharmaceutically acceptable salt, solvate, or prodrug thereof), formulated with a pharmaceutically acceptable excipient, and typically manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

In another embodiment, the invention relates to synergistic nutritional composition which can be prepared in a manner well known in the pharmaceutical art, and can be administered by a variety of routes, depending upon whether local or systemic treatment is desired and upon the area to be treated. Administration may be oral, topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Particularly the composition can be administered to subject in a form suitable for oral use, such as a tablet, (in delayed release or extended release or sustained release or enteric coated release system) chewable tablets, effervescent tablets capsule, vegetable capsule such as HPMC capsule, polysaccharide capsule, gelatin capsule such as hard gelatin capsule, soft gelatin capsule, encapsulate, matrix, coat, beadlets, nanoparticles, caplet, particulate, agglomerate, spansule, lozenge, troche, solution, suspension, rapidly dissolving film, elixir, gel, aqueous or oily solution, suspension or emulsion; for sub-lingual or buccal use, in the form of powder, granule, tablet shapes (including sphere, round concave oval, and triangular), a pill, capsule or the like in the form of a solid, or emulsion, a paste, a jelly-like, such as a solution (in the form of a drink and the like) can be prepared in the form of solutions, sprays or reconstituted dry powdered form with a liquid medium or syrup.

An effective dose is a dose that produces a desirable clinical outcome by, for example, improving a sign or symptom of endothelial dysfunction. Accordingly, the effective unit dose can be formulated in the range of 100 to 750 mg, preferably 150-500 mg and administered daily once or twice or thrice based on the type of endothelial dysfunction.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof and, accordingly, reference should be made to the appended claims, rather than to the foregoing specification, as indicating the scope of the invention.

The invention may be further illustrated by the following examples, which are for illustrative purposes only and should not be construed as limiting the scope of the invention in anyway.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes or alterations which come within the ambit of equivalency are intended to be encompassed therein.

EXAMPLES

Example 1

Composition 1a: Synergistic Blend

| Ingredient | w/w % |
| --- | --- |
| $N^1$-Methyl nicotinamide chloride | 5-50% |
| Standardized Red Spinach Extract (*Amaranthus cruentus*) (with nitrate content not less than 9.0%) | 30-90% |

Composition 1b: Synergistic Blend

| Ingredient | w/w % |
| --- | --- |
| $N^1$-Methyl nicotinamide chloride | 20 ± 5% |
| Standardized Red Spinach Extract (*Amaranthus cruentus*) (with nitrate content not less than 9.0%) | 80 ± 5% |

Composition 1c: Synergistic Blend

| Ingredient | w/w % unit dose |
| --- | --- |
| $N^1$-Methyl nicotinamide chloride | 30 ± 5% |
| Standardized Red Spinach Extract (*Amaranthus cruentus*) (with nitrate content not less than 9.0%) | 70 ± 5% |

Composition 2: Tablet/Capsule

| Ingredient | w/w % unit dose |
| --- | --- |
| $N^1$-Methyl nicotinamide chloride | 20 ± 5% |
| Standardized Red Spinach Extract (*Amaranthus cruentus*) (with nitrate content 9.24%) | 70 ± 5% |
| Excipients | 10 ± 5% |
| Average Wt | 100% |
| Average wt in mg | 150-250 mg |

Composition 3: Tablet/Capsule

| Ingredient | w/w % unit dose |
| --- | --- |
| $N^1$-Methyl nicotinamide chloride | 15 ± 5% |
| Standardized Red Spinach Extract (*Amaranthus cruentus*) (with nitrate content 9.24%) | 65 ± 5% |
| Excipients | 20 ± 5% |
| Average Wt | 100% |
| Average wt in mg | 250-350 mg |

Composition 4: Tablet/Capsule

| Ingredient | w/w % unit dose |
| --- | --- |
| $N^1$-Methyl nicotinamide chloride | 10 ± 5% |
| Standardized Red Spinach Extract (*Amaranthus cruentus*) (with nitrate content 9.24%) | 40 ± 5% |
| Excipients | 40 ± 5% |
| Average Wt | 100% |
| Average wt in mg | 400-500 mg |

Composition 5: Tablet/Capsule

| Ingredient | w/w % unit dose |
| --- | --- |
| $N^1$-Methyl nicotinamide chloride | 10-20% |
| Standardized Red Spinach Extract (*Amaranthus cruentus*) (with nitrate content 9.24%) | 50-75% |
| Diluents | 1-10% |
| Binders | 0.5-5% |
| Glidants | 0.5-5% |
| Lubricants | 0.5-5% |
| Additives | 1-10% |
| Solvents | QS |

Composition 6: Tablet/Capsule

| Ingredient | w/w % unit dose |
| --- | --- |
| $N^1$-Methyl nicotinamide chloride | 15-30% |
| Standardized Red Spinach Extract (*Amaranthus cruentus*) (with nitrate content 9.24%) | 35-70% |
| Diluents | 1-20% |
| Binders | 0.5-5% |
| Glidants | 0.5-5% |
| Lubricants | 0.5-5% |
| Additives | 1-10% |
| Solvent | QS |

Composition 7: Tablet/Capsule

| Ingredient | mg per unit dose |
| --- | --- |
| $N^1$-Methyl nicotinamide chloride | 45 |
| Standardized Red Spinach Extract (*Amaranthus cruentus*) (with nitrate content 9.24%) | 206 |
| Microcrystalline Cellulose | 1-20 |
| Silicon dioxide | 1-15 |
| Hydroxypropyl Methylcellulose | 2-10 |
| Zinc Stearate | 2-10 |
| PVP K-30 | 5-10 |
| Talc | 1-10 |
| Polysorbate 80 | 1-20 |
| Mannitol | 5-20 |
| IPA | QS |
| Water | QS |
| Average weight | 250-350 mg |

Composition 8: Tablet/Capsule

| Ingredient | mg per unit dose |
| --- | --- |
| $N^1$-Methyl nicotinamide chloride | 45 |
| Standardized Red Spinach Extract (*Amaranthus cruentus*) (with nitrate content 9.24%) | 103 |
| Microcrystalline Cellulose | 2-20 |
| Silicon dioxide | 1-15 |
| Hydroxypropyl Methylcellulose | 2-10 |
| Magnesium Stearate | 1-10 |
| PVP K-30 | 5-10 |
| Talc | 1-10 |
| Tween 80 | 1-20 |
| Mannitol | 1-25 |
| IPA | QS |
| Water | QS |
| Average weight | 150-250 mg |

The present composition is stable for 06 months under the accelerated condition [40° C., 75% RH], where the purity of the active ingredients is above 96%.

Example 2

Modulatory effect of the test substances on PGI2 gene by gene expression method

The test substances were evaluated for its gene expression activity in H9C2 (rat cardiomyocytes), the concentration of test substances (G1, G2 and G3) is 500 µg/ml were taken for gene expression studies. In gene expression study the test substance, at higher concentration showed up-regulation in the level of gene as compared to the control tissue. [*Hunter C. Champion et al. PNAS,* 2005; 102:5:1661-1666].

In this study, test substances were divided into (03) groups.
Nitroglycerin served as standard sample;
Group 1 (G1) served as $N^1$-methyl nicotinamide chloride;
Group 2 (G2) served as Standardized red spinach extract with nitrate content 9.24%, and
Group 3 (G3) served as served as composition 1a.

Method

Outline of the Method

PGI2 were estimated for the test substance by gene expression method, where the level of expression of PGI2 expression on Rat Cardiomyocytes (H9C2) was determined with respect to untreated H9C2 cells.

RNA Isolation and cDNA Synthesis

The H9C2 cells treated with drug were subjected to cell lysis by treating with Tri-extraction reagent. Chloroform was added, to isolate the total RNA from the sample and subjected for centrifugation. Out of the three distinct layers observed, upper layer was collected in fresh tube and equal volume of isopropanol was added and incubated at −20° C. for 10 mins. After the incubation followed by centrifugation, appropriate volume of ethanol was added to resuspend the pellet. After incubation and centrifugation, the pellet was air dried and appropriate volume of TAE buffer was added. The isolated total RNA was further used for cDNA synthesis. cDNA was synthesized by priming with oligo-dT primers followed by reverse transcriptase enzyme treatment according to manufacturers protocol (Thermoscienctific). The cDNA thus synthesized was taken up for PCR for the amplification of $PGI_2$ and GAPDH/β-Actin (internal control).

RT-PCR Procedure

The mRNA expression levels of $PGI_2$ were determined using semi-quantitative reverse transcriptase-polymerase chain reaction (RT-PCR). 50 µl of the reaction mixture was subjected to PCR for amplification of $PGI_2$. cDNAs using specifically designed primers procured from Eurofins, India and GAPDH/β-Actin (House keeping genes) was co-amplified with each reaction as an internal control.

Amplification Conditions for $PGI_2$ Gene $PGI_2$: 95° C. for 5 min followed by 35 cycles of denaturation at 95° C. for 30 seconds, annealing Tm for 30 seconds and extension at 72° C. for 45 seconds. This was followed by final extension at 72° C. for 10 min. The primers used in this example for I strand synthesis and IInd strand synthesis are disclosed in priority Indian Patent Application No. 201921000093, filed Jan. 2, 2019, which is incorporated herein by reference.
Product size: 269 bp.
Results

TABLE 2

The gene expression level of PGI$_2$ normalized to GAPDH of G1, G2, G3 treated cells.

| Test Sample | Regulation in Terms of Folds* PGI$_2$ | PGI2 expression in % |
|---|---|---|
| Control | 1.00 | ... |
| Nitroglycerin (250 µg/ml) | 1.29 | 29% |
| G1 | 1.14 | 14% |
| G2 | 1.12 | 12% |
| G3 | 1.27 | 27% |

*Values shown in term of the fold.

Discussion and Conclusion

The test substances G1, G2 and G3 were evaluated for PGI2 gene expression activity in H9C2. When the level of mRNA expression was analyzed by reverse transcriptase PCR, it was observed that Prostacyclin gene (PGI2) expression increased with G1, G2 and G3 by 0.14 folds, 0.12 folds and 0.27 folds respectively at concentration of 500 µg/ml in H9C2 cells, as compared to the control.

In brief, test substances showed up-regulated PGI2 gene expression level in H9C2. The instant composition G3 shows synergistic effect as compared to individual actives G1 and G2.

Example 3

Modulatory Effect of the Test Substances on eNOS Gene by Gene Expression Method

The test substances were evaluated for their gene expression activity in H9C2 (rat cardiomyocytes) and the concentration of test substances (G1, G2 and G3) taken for gene expression studies was 500 µg/ml. In gene expression study the test substance, at higher concentration showed up-regulation in the level of eNOS gene as compared to the control tissue. [Hunter C. Champion, et al. "*PNAS*, 2005; 102:5:1661-1666.]
Method
Outline of the Method eNOS levels were estimated for the test substance by gene expression method, where the level of expression of eNOS expression on Human Cardiomyocytes (H9C2) was determined with respect to untreated H9C2 cells.
RNA Isolation and cDNA Synthesis The H9C2 cells treated with test samples were subjected to cell lysis by treating with Tri-extraction reagent. Chloroform was added to isolate the total RNA from the sample and subjected for centrifugation. Out of the three distinct layers observed, upper layer was collected in fresh tube and equal volume of isopropanol was added and incubated at −20° C. for 10 mins. After the incubation followed by centrifugation, appropriate volume of ethanol was added to resuspend the pellet. After incubation and centrifugation, the pellet was air dried and appropriate volume of TAE buffer was added. The isolated total RNA was further used for cDNA synthesis. cDNA was synthesized by priming with oligo-dT primers followed by reverse transcriptase enzyme treatment according to manufacturer's protocol (Thermoscienctific). The cDNA thus synthesized was taken up for PCR for the amplification of eNOS and GAPDH (internal control).
RT-PCR Procedure The mRNA expression levels of eNOS were determined using semi-quantitative reverse transcriptase-polymerase chain reaction (RT-PCR). 50 µl of the reaction mixture was subjected to PCR for amplification of eNOS. cDNAs using specifically designed primers procured from Eurofins, India and GAPDH/β-Actin (House keeping genes) was co-amplified with each reaction as an internal control.
Amplification Conditions for eNOS Gene eNOS: 95° C. for 5 min followed by 35 cycles of denaturation at 95° C. for 30 seconds, annealing temperature for 30 seconds and extension at 72° C. for 45 seconds. This was followed by final extension at 72° C. for 10 min. The primers used in this example for I strand synthesis and IInd strand synthesis are disclosed in priority Indian Patent Application No. 201921000093, filed Jan. 2, 2019, which is incorporated herein by reference.
Product size: 715 bp.
Result

TABLE 3

The gene expression level of eNOS normalized to β-Actin of G1, G2, G3 treated cells.

| Test Sample | Regulation in Terms of Folds* eNOS | eNOS expression in % |
|---|---|---|
| Control | 1.00 | ... |
| Standard Nitroglycerin (250 µg/ml) | 1.56 | 56% |
| G1 | 1.21 | 21% |
| G2 | 1.39 | 39% |
| G3 | 1.46 | 46% |

*Values shown in term of the fold.

Discussion and Conclusion

The test substance, G1, G2 and G3 were evaluated for its modulatory effect on eNOS gene expression in H9C2. The level of mRNA expression was analyzed by reverse transcriptase PCR. TNF-alpha was employed as positive control for the eNOS gene expression. Endothelial nitric oxide synthase gene (eNOS) expression was over expressed by the treatment with G1, G2 and G3 by 0.21, 0.39 and 0.46 folds at tested doses in H9C2 cells, respectively as compared to the control. The present composition G3 exhibited enhancement of eNOS expression by 0.46 folds over control, where the standard sample (Nitroglycerin) up-regulated the eNOS gene expression by 0.56 fold over control.

Among the test substances, present composition G3 showed greater up-regulation of eNOS expression.

We claim:

1. A method of treatment of endothelial dysfunction in a subject in need thereof, wherein the method comprising, oral administration of a therapeutically effective amount of a nutritional composition comprising a synergistic blend of N-1 methyl nicotinamide chloride and standardized red amaranth extract enriched with 9-12% by weight nitrate content with pharmaceutically acceptable excipients,
    wherein the N-1 methyl nicotinamide chloride and the standardized red amaranth extract enriched with nitrate content are present in a weight ratio of 1:1 to 1:6; and the N-1 methyl nicotinamide chloride and the nitrate content of the standardized red amaranth extract are present in a weight ratio of 1:0.1 to 1:0.6.

2. The method of treatment according to claim 1, wherein the N-1 methyl nicotinamide chloride is present in a range of 5.0% to 50.0% by weight of the total composition.

3. The method of treatment according to claim 1, wherein the standardized red amaranth extract enriched with nitrate content is present in a range of 30.0% to 90.0% by weight of the total composition.

4. The method of treatment according to claim 1, wherein the nitrate content of the standardized red amaranth extract is present in the range of 9.0% to 12.0% by weight of the standardized red amaranth extract and 2.0 to 10.0% by weight of the total composition.

5. The method of treatment according to claim 1, wherein the red amaranth extract is an aqueous extract of *Amaranthus cruentus* leaves.

6. The method of treatment according to claim 1, wherein the endothelial dysfunction is selected from the group consisting of arteriosclerosis, chronic kidney disease (CKD), high blood pressure, lipid metabolism, diabetes, ulcer, obesity, metabolic syndrome, coronary artery disease, cerebrovascular disease, disseminated intravascular coagulation syndrome (DIC), aortic diseases, cardiovascular dysfunction, coronary artery disease (CAD), hypertension, microvascular angina, diastolic dysfunction, peripheral vascular disease (PAD), thrombosis, stroke, myocardial ischemia or infarction and dyslipidemia.

7. The method of treatment according to claim 1, wherein the endothelial dysfunction is myocardial ischemia or infarction.

8. The method of treatment according to claim 1, wherein the composition exhibits increased level of PGI2 expression by 0.27 folds over control.

9. The method of treatment according to claim 1, wherein the composition exhibits increased level of eNOS expression by 0.46 folds over control.

* * * * *